(12) United States Patent
Mujawar et al.

(10) Patent No.: US 12,413,843 B2
(45) Date of Patent: Sep. 9, 2025

(54) SYSTEM AND METHOD OF PATIENT REGISTRATION

(71) Applicant: Medtronic Navigation, Inc., Louisville, CO (US)

(72) Inventors: Arifmohamd Hamaju Mujawar, Sangli (IN); Manisha Chalamalasetti, Pragathi Nagar (IN); Jyothi Bonthu, Hyderabad (IN); Praveena Narayanabhatla, Hyderabad (IN); Pratima Mehta, Hyderabad (IN)

(73) Assignee: Medtronic Navigation, Inc., Louisville, CO (US)

( * ) Notice: Subject to any disclaimer, the term of this patent is extended or adjusted under 35 U.S.C. 154(b) by 182 days.

(21) Appl. No.: 18/297,153

(22) Filed: Apr. 7, 2023

(65) Prior Publication Data
US 2024/0340521 A1  Oct. 10, 2024

(51) Int. Cl.
*H04N 23/611* (2023.01)

(52) U.S. Cl.
CPC ................................. *H04N 23/611* (2023.01)

(58) Field of Classification Search
None
See application file for complete search history.

(56) References Cited

U.S. PATENT DOCUMENTS

| | | | |
|---|---|---|---|
| 5,592,939 A | 1/1997 | Martinelli | |
| 5,913,820 A | 6/1999 | Bladen et al. | |
| 5,983,126 A | 11/1999 | Wittkampf | |
| 6,474,341 B1 | 11/2002 | Hunter et al. | |
| 6,684,093 B2 | 1/2004 | Kuth | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,751,865 B2 | 7/2010 | Jascob et al. | |
| 11,141,237 B2 | 10/2021 | Gregersen et al. | |
| 2004/0199072 A1 | 10/2004 | Sprouse et al. | |
| 2005/0085720 A1 | 4/2005 | Jascob et al. | |
| 2008/0097195 A1 | 4/2008 | Urquhart et al. | |
| 2008/0269599 A1 | 10/2008 | Csavoy et al. | |
| 2011/0098553 A1 | 4/2011 | Robbins et al. | |
| 2019/0192228 A1* | 6/2019 | Salazar | A61B 90/13 |
| 2021/0056699 A1 | 2/2021 | Srimohanarajah et al. | |
| 2021/0304423 A1 | 9/2021 | Yi et al. | |
| 2022/0167868 A1* | 6/2022 | Sela | A61B 34/20 |

FOREIGN PATENT DOCUMENTS

CA  2917654 C  9/2018

OTHER PUBLICATIONS

International Search Report and Written Opinion of the ISA issued in PCT/US2024/023286, mailed Jun. 17, 2024; ISA/US.

* cited by examiner

*Primary Examiner* — Xiaolan Xu
(74) *Attorney, Agent, or Firm* — Mueting Raasch Group

(57) ABSTRACT

Disclosed is a system to register a subject, e.g., physical, space to an image space. The registration may be performed automatically by a registration system with a registration device. The registration device may acquire an image of a subject space.

18 Claims, 10 Drawing Sheets

SYSTEM AND METHOD OF PATIENT REGISTRATION

FIELD

The present disclosure relates to a surgical navigation system, and particularly to a method for registering a patient pre- and intra-operatively to an image data.

BACKGROUND

The statements in this section merely provide background information related to the present disclosure and may not constitute prior art.

In image-guided surgery for glioma removal, neurosurgeons usually plan the resection on images acquired before surgery and use them for guidance during the subsequent intervention. After the surgical procedure has begun, the pre-planning images may become unreliable due to a brain shift phenomenon, caused by modifications of anatomical structures and imprecisions in the neuronavigational system. Brain shift is when the brain moves relative to a skull.

In the current standard of care, the manual intervention from the surgeon may be required to complete the registration process which is required before the start of surgical procedure. It is desirable to avoid the manual intervention in the registration process and to enhance the accuracy of the registration.

SUMMARY

To obtain an updated view of the resection cavity, one solution is to collect intraoperative data using a registration process, which can be additionally acquired at different stages of the procedure in order to provide a better understanding of the resection.

An image, which may be a pre-procedure image, may be acquired of the subject. The image may define an image space. A position of an instrument relative to a subject that has been imaged may be determined with a tracking system. The position of the instrument may be displayed relative to the acquired image due to a registration of a subject space to the image space.

The registration may occur by determining the position of various points on the subject and correlating them to points in the image space. The correlation may allow for a determination and generation of a translation map between the physical or subject space of the subject and the image space of the image. Once the registration is completed the tracked position of an instrument may be displayed relative to the image.

During a procedure, a subject may be registered. The registration may be substantially automatic by a registration system. The registration system may acquire a registration image of the subject. Further during a procedure an automatic or updated registration may occur due to a determination that the subject has moved in the registration system may again register the subject space to the image space.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Although the following description illustrates and describes a procedure relative to a cranium of a patient, the current disclosure is not to be understood to be limited to such a procedure. For example, a procedure can also be performed relative to a spinal column, heart, vascular system, etc. Therefore, discussion herein relating to a specific region of the anatomy will be understood to be applicable to all regions of the anatomy, unless specifically described otherwise.

As discussed herein, various systems and elements can be used to assist in a surgical procedure. For example, image data can be acquired of a patient to assist in illustrating a location of an instrument relative to a patient. Generally, image space (i.e., defined by a coordinate system of an image generated or reconstructed from image data) can be registered to patient space (i.e., defined by a coordinate system of a physical space relative to a patient to assist in this display and navigation.

Figure 1:
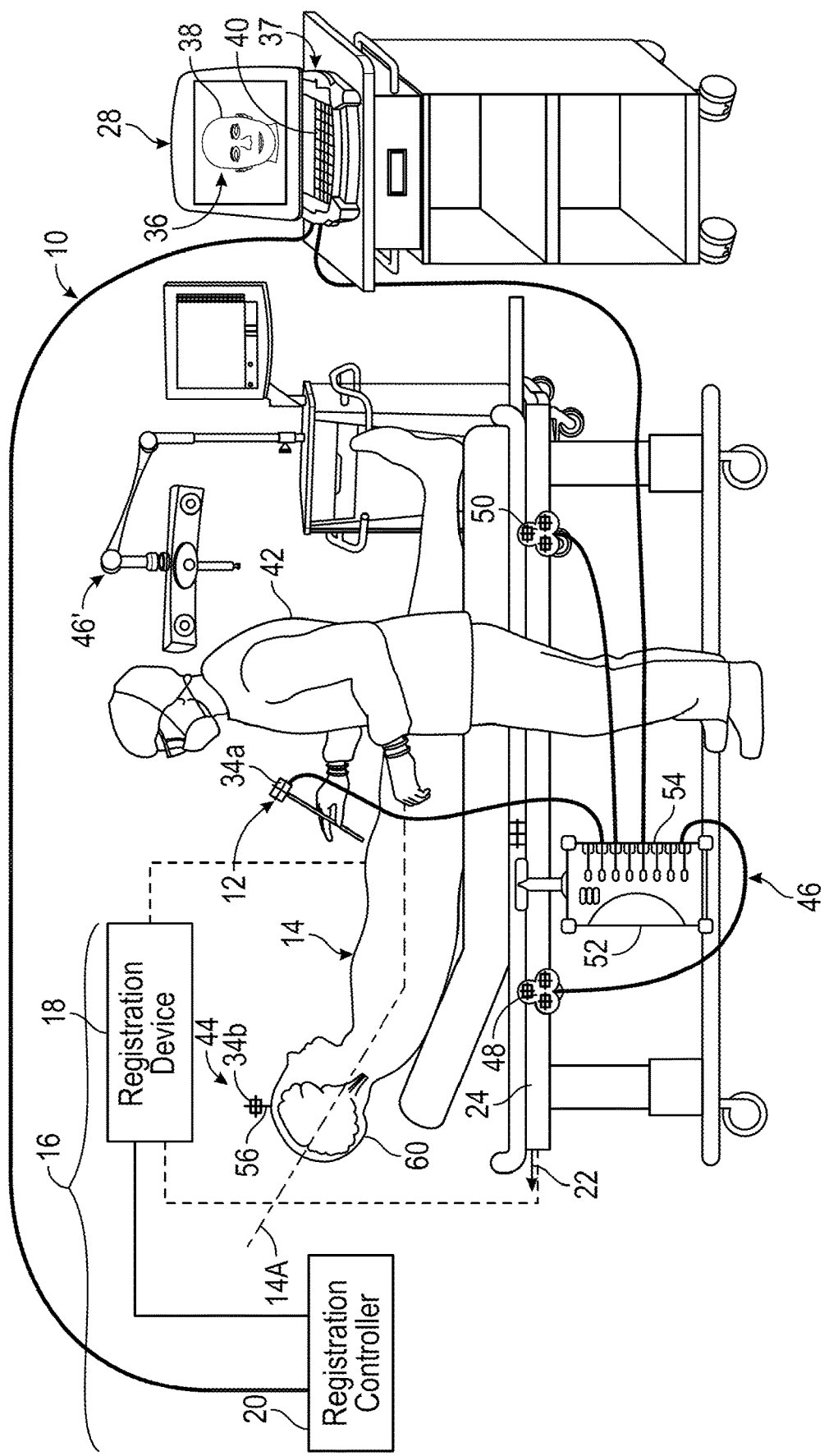
FIG. 1 is an environmental view of a surgical navigation system or computer aided surgical system, according to various embodiments.

With reference to FIG. 1, a navigation system 10 that can be used for various procedures is illustrated. The navigation system 10 can be used to track the location of a device 12, such as a pointer probe, relative to a patient 14 to assist in the implementation or performance of a surgical procedure. It should be further noted that the navigation system 10 may be used to navigate or track other devices including: catheters, probes, needles, leads, electrodes implants, etc. According to various embodiments, examples include ablation catheters, deep brain stimulation (DBS) leads or electrodes, micro-electrode (ME) leads or electrodes for recording, etc. Moreover, the navigated device may be used in any region of the body. The navigation system 10 and the various devices may be used in any appropriate procedure, such as one that is generally minimally invasive, arthroscopic, percutaneous, stereotactic, or an open procedure. Although an exemplary navigation system 10 including an image registration system 16 are discussed herein, one skilled in the art will understand that the disclosure is merely for clarity of the present discussion and any appropriate imaging system, navigation system, patient specific data, and non-patient specific data can be used. It will be understood that the navigation system 10 can incorporate or be used with any appropriate preoperatively or intraoperatively acquired image data.

The navigation system 10 includes the image registration system 16 used to acquire and compare pre- and intra-operative, including real-time image data of the patient 14 without using separate implanted or attached fiducial markers. In various embodiments, the system may register and/or maintain registration to intra-operatively acquired image data. In various embodiments, the system may register and/or maintain registration to pre-operative image data until the end of the procedure or until movement, such as skull movement, is detected. If movement is detected, such as with the distance sensors as discussed herein, the registration is maintained by allowing a re-registration.

The registration system 16 may, for example, use visible light, infrared, or thermal technologies emitted from a registration device 18 which in turn transmits an image to a registration controller 20. The registration controller 20 may control the position of the registration device 18 by way of actuators as further described below in the examples set forth. The registration controller 20 ultimately determines data that corresponds to various physical features of the patient, distance, or positions of the features as described in detail below used for registration. In various embodiments, this data may relate to discussion markers and/or points. The image from the registration device 18 may include information, as discussed herein, that is useful for registration to an image of the subject acquired with an imaging system, as discussed herein. The image data of the subject may be pre- or intra-operative image data. The image data may be used to generate an image that is displayed.

In the example of FIG. 1, the longitudinal axis 14A of the patient 14 is substantially in line with the longitudinal axis 22 of the operating table 24. In this example, the upper body of the patient 14 is elevated but the longitudinal axes 14A and 22 are aligned.

Fiducial marker or point data useful for registration obtained from the image of the registration system 16 can then be forwarded to the navigation computer and/or processor controller or workstation 28 having a display device 36 to display image data 38 and a user interface 40. Workstation 28 may also have an audible device 37 such as a speaker, buzzer or vibration generator for generating an audible signal. The display device 36 and/or the display may generate a visual and/or audible signal corresponding to a registration or a lack of registration of a patient space to an image space which is described in more detail below. The workstation 28 can also include or be connected to an image processor, a navigation processor, and a memory to hold instruction and data. It will also be understood that the image data is not necessarily retained in the controller 20 but may also be directly transmitted to the workstation 28. Moreover, processing for the navigation system and optimization can all be done with a single or multiple processors all of which may or may not be included in the workstation 28. For example, the registration controller 20 may be incorporated into the workstation 28.

The workstation 28 provides facilities for displaying the image data 38 as an image on the display device 36, saving, digitally manipulating, or printing a hard copy image of the received image data. The user interface 40, which may be a keyboard, mouse, touch pen, touch screen or other suitable device, allows a physician or user 42 to provide inputs to control the imaging system 16 or adjust the display settings of the display device 36. The workstation 28 may also direct registration device 18 to adjust the position relative to the patient 14.

With continuing reference to FIG. 1, the navigation system 10 can further include a tracking system, such as, but not limited to, an electromagnetic (EM) tracking system 46 or an optical tracking system 46'. Either or both can be used alone or together in the navigation system 10. The discussion herein of the EM tracking system 46 can be understood to relate to any appropriate tracking system. The optical tracking system 46' can include the StealthStation® Treon® and the StealthStation® Tria® both sold by Medtronic Navigation, Inc. Other tracking system modalities may include acoustic, radiation, radar, infrared, etc.

The EM tracking system 46 includes a localizer, such as a coil array 48 and/or second coil array 50, a coil array controller 52, a navigation probe interface 54, the device 12 (e.g., instrument, tool, catheter, needle, pointer probe, or instruments, as discussed herein) and a dynamic reference frame (DRF) 44. An instrument tracking device 34a can also be associated with, such as fixed to, the device 12 or a guiding device for an instrument. The dynamic reference frame 44 can include a dynamic reference frame holder 56 and a removable tracking device 34b. Alternatively, the dynamic reference frame 44 can include the tracking device 34b that can be formed integrally or separately from the DRF holder 56.

Moreover, the DRF 44 can be provided as separate pieces and can be positioned at any appropriate position on the anatomy. For example, the tracking device 34b of the DRF can be fixed to the skin of the patient 14 with an adhesive. Also, the DRF 44 can be positioned near a leg, arm, etc. of the patient 14. Thus, the DRF 44 does not need to be provided with a head frame or require any specific base or holding portion.

The tracking devices 34, 34a, 34b or any tracking device as discussed herein, can include a sensor, a transmitter, or combinations thereof. Further, the tracking devices can be wired or wireless to provide a signal emitter or receiver within the navigation system. For example, the tracking device can include an electromagnetic coil to sense a field produced by the localizing array 48, 50 or reflectors that can reflect a signal to be received by the optical tracking system 46'. Nevertheless, one will understand that the tracking device can receive a signal, transmit a signal, or combinations thereof to provide information to the navigation system 10 to determine a location of the tracking device 34, 34a, 34b. The navigation system 10 can then determine the position of the instrument or tracking device to allow for navigation relative to the patient and patient space.

The coil arrays 48, 50 may also be supplemented or replaced with a mobile localizer. The mobile localizer may be one such as that described in U.S. patent application Ser. No. 10/941,782, filed Sep. 15, 2004, now U.S. Pat. App. Pub. No. 2005/0085720, entitled "METHOD AND APPARATUS FOR SURGICAL NAVIGATION", herein incorporated by reference. As is understood the localizer array can transmit signals that are received by the tracking devices 34, 34a, 34b. The tracking devices 34, 34a, 34b can then transmit or receive signals based upon the transmitted or received signals from or to the array 48, 50.

Further included in the navigation system 10 may be an isolator circuit or assembly (not illustrated separately). The isolator circuit or assembly may be included in a transmission line to interrupt a line carrying a signal or a voltage to the navigation probe interface 54. Alternatively, the isolator circuit included in the isolator box may be included in the navigation probe interface 54, the device 12, the dynamic reference frame 44, the transmission lines coupling the devices, or any other appropriate location. The isolator assembly is operable to isolate any of the instruments or patient coincidence instruments or portions that are in contact with the patient should an undesirable electrical surge or voltage take place.

It should further be noted that the entire tracking system 46, 46' or parts of the tracking system 46, 46' may be incorporated into the registration system 16, including the workstation 28. Incorporating the tracking system 46, 46' may provide an integrated imaging and tracking system. This can be particularly useful in creating a fiducial-less system without separate physical or implanted markers attached to the patient. Moreover, fiducial marker-less systems can include a tracking device and a contour determining system, including those discussed herein.

The EM tracking system 46 uses the coil arrays 48, 50 to create an electromagnetic field used for navigation. The coil arrays 48, 50 can include a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 48 is controlled or driven by the coil array controller 52. The coil array controller 52 drives each coil in the coil array 48 in a time division multiplex or a frequency division multiplex manner. In this regard, each coil may be driven separately at a distinct time or all of the coils may be driven simultaneously with each being driven by a different frequency.

Upon driving the coils in the coil array 48 with the coil array controller 52, electromagnetic fields are generated within the patient 14 in the area where the medical procedure is being performed, which is again sometimes referred to as patient space. The electromagnetic fields generated in the patient space induce currents in the tracking device 34, 34*a*, 34*b* positioned on or in the device 12, DRF 44, etc. These induced signals from the tracking devices 34, 34*a*, 34*b* are delivered to the navigation probe interface 54 and subsequently forwarded to the coil array controller 52. The navigation probe interface 54 can also include amplifiers, filters and buffers to directly interface with the tracking device 34*b* attached to the device 12. Alternatively, the tracking device 34*b*, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 54.

Various portions of the navigation system 10, such as the device 12, the dynamic reference frame 44, are equipped with at least one, and generally multiple, EM or other tracking devices 34*a*, 34*b*, that may also be referred to as localization sensors. The EM tracking devices 34*a*, 34*b* can include one or more coils that are operable with the EM localizer arrays 48, 50. An alternative tracking device may include an optical device, and may be used in addition to or in place of the electromagnetic tracking devices 34*a*, 34*b*. The optical tacking device may work with the optional optical tracking system 46'. One skilled in the art will understand, however, that any appropriate tracking device can be used in the navigation system 10. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

In brief, the EM tracking device 34*a* on the device 12 can be in a handle or inserter that interconnects with an attachment and may assist in placing an implant or in driving a member. The device 12 can include a graspable or manipulable portion at a proximal end and the tracking device 34*a* may be fixed near the manipulable portion of the device 12 or at a distal working end, as discussed herein. The tracking device 34*a* can include an electromagnetic tracking sensor to sense the electromagnetic field generated by the coil array 48, 50 that can induce a current in the electromagnetic device 34*a*. Alternatively, the tracking device 34*a* can be driven (i.e., like the coil array above) and the tracking array 48, 50 can receive a signal produced by the tracking device 34*a*.

The dynamic reference frame 44 may be fixed to the head 60 of the patient 14 adjacent to the region being navigated so that any movement of the patient 14 is detected as relative motion between the coil array 48, 50 and the dynamic reference frame 44. The dynamic reference frame 44 can be interconnected with the patient in any appropriate manner, including those discussed herein. Relative motion is forwarded to the coil array controller 52, which updates registration correlation and maintains accurate navigation, further discussed herein. The dynamic reference frame 44 may include any appropriate tracking device. Therefore, the dynamic reference frame 44 may also be EM, optical, acoustic, etc. If the dynamic reference frame 44 is electromagnetic it can be configured as a pair of orthogonally oriented coils, each having the same center or may be configured in any other non-coaxial or co-axial coil configurations.

Briefly, the navigation system 10 operates as follows. The navigation system 10 creates a map of points, which may include all points, in the image data generated from the registration device 18 which can include external and internal portions that correspond to points in the patient's anatomy in patient space. This map generated with the registration device 18 may then be translated (e.g., a translation map is made) to image data acquired for the subject 14, such as pre- or intra-operatively. After this translation map is established, whenever the tracked device 12 is used, the workstation 28 in combination with the coil array controller 52 uses the translation map to identify the corresponding point on the image data or atlas model, which is displayed on display 36, and may be the pre- or intra-operatively image data. This identification is known as navigation or localization. An icon representing the localized point of the instruments is shown on the display 36 in an appropriate manner, such as within one or several two-dimensional image planes, as well as on three- and four-dimensional images and models.

To enable navigation, the navigation system 10 must be able to detect both the position of the patient's anatomy and the position of the device 12 or an attachment member (e.g., tracking device 34*a*) attached to the device 12. Knowing the location of these two items allows the navigation system 10 to compute and display the position of the device 12 or any portion thereof in relation to the patient 14. The tracking system 46 is employed to track the device 12 and the anatomy of the patient 14 simultaneously.

The tracking system 46, if it is using an electromagnetic tracking assembly, essentially works by positioning the coil array 48, 50 adjacent to the patient 14 to generate a magnetic field, which can be low energy, and generally referred to as a navigation field. Because every point in the navigation field or patient space is associated with a unique field strength, the electromagnetic tracking system 46 can determine the position of the device 12 by measuring the field strength at the tracking device 34a location. The dynamic reference frame 44 is fixed to the patient 14 to identify the location of the patient in the navigation field. The electromagnetic tracking system 46 continuously computes or calculates the relative position of the dynamic reference frame 44 and the device 12 during localization and relates this spatial information to patient registration data to enable navigation of the device 12 within and/or relative to the patient 14. Navigation can include image guidance or imageless guidance.

The points that are selected to perform registration can be image anthropometric points compared as registration is taking place. The image points can be anatomical landmarks, measurements between landmarks and combinations thereof as described in more below. The landmarks are identifiable in the image data and identifiable and accessible on the patient 14. The anatomical landmarks can include individual or distinct points on the patient 14 or contours (e.g., three-dimensional contours) defined by the patient 14.

As discussed above, registration of the patient space or physical space to the image data or image space can require the correlation or matching of physical or virtual fiducial points observed intra-operational and the image fiducial points of pre-operative images. The physical fiducial points in the present example are anatomical landmarks in the substantially fiducial marker-less systems. The physical fiducial points can also include a determined contour (e.g., a physical space 3D contour) using various techniques, as discussed herein.

The image fiducial marker-less points in the image data can also be determined. The user 42 can locate the image fiducial points by imagining the anthropometric points. Also, various algorithms are generally known to determine the location of the image fiducial points. The image fiducial points can be produced in the image data of the patient 14 during acquisition of the image data.

Once the marker-less image fiducial points have been identified, the image space and the physical space can be registered. A processor, such as a processor within the workstation 28, can determine registration of the patient space to the image space. The registration can be performed according to generally known mapping or translation techniques. The registration can allow a navigated procedure using the image data. A description of two examples of a system not requiring separate implanted or body mounted physical fiducial markers is set forth below.

Figure 2A:
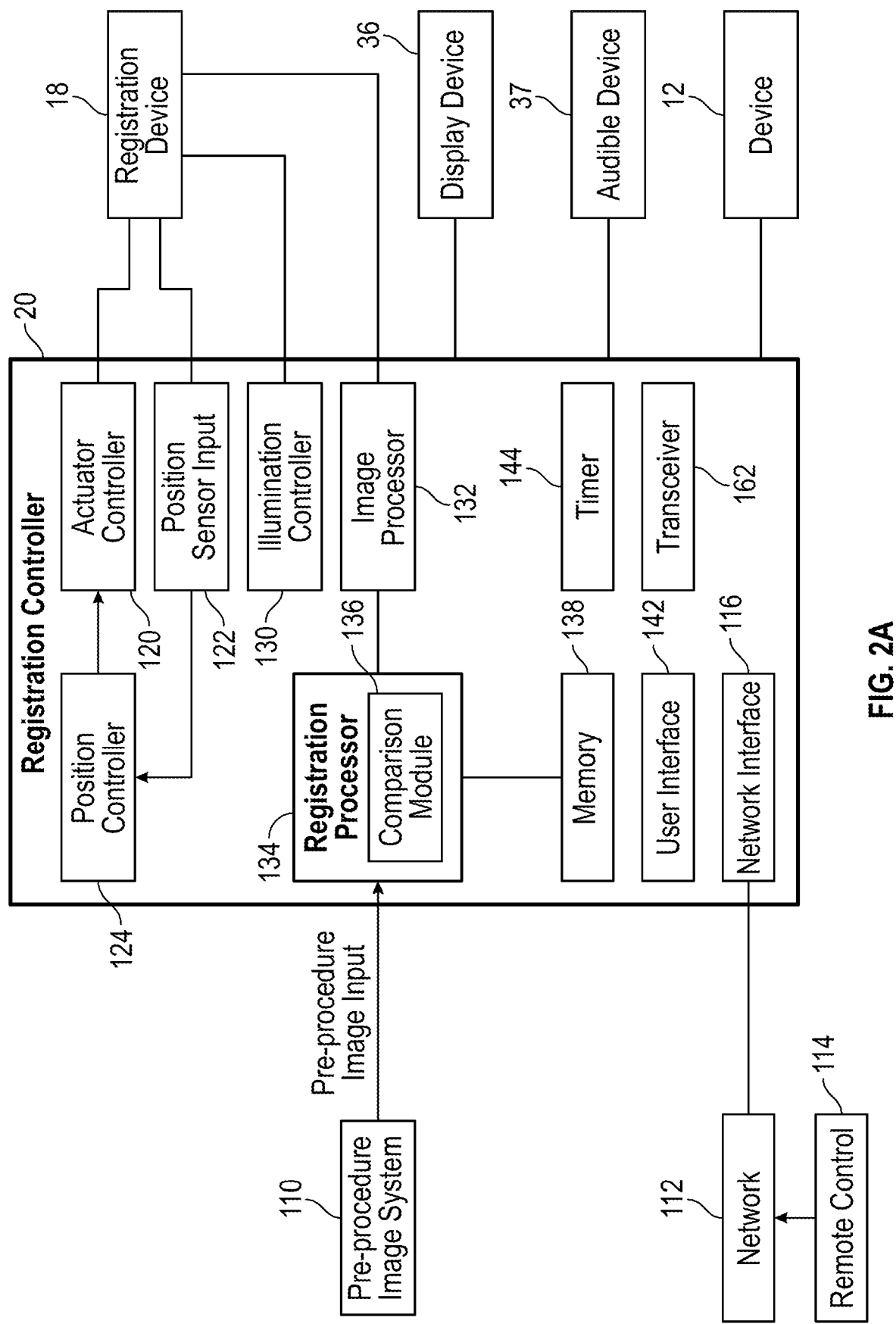
FIG. 2A is a high level block diagram of the registration controller of FIG. 1.

Referring now to FIG. 2A, details of the registration controller 20 are illustrated. As mentioned above, the registration controller 20 may be a separate computer or device or may be incorporated into the workstation 28. The registration controller 20 may acquire selected image data, such as pre-procedure image data and may be in communication with a pre-procedure image system 110. The pre-procedure image system 110 may include, but is not limited to, a computed tomography (CT) system generating a CT image, an X-Ray system generating an X-ray image, O-Arm® imaging system, an MRI system generating an MRI image, or an ultrasound system generating an ultrasound image. One example of a pre-procedure image system is set forth below in FIG. 2C. The pre-procedure image system 110 may obtain pre-procedure images that are provided to the registration controller 20 for comparison with an intraoperative image. The pre-procedure image system 110 may provide a digital image file to the registration controller 20.

The registration controller 20 may also be in communication with a network 112. The network 112, such as the Internet, may have a wired or wireless network connection. Various types of data may be communicated through the network 112 including from a remote control 114 that may be used to operate the system. The remote control 114 may be a separate component or a component integrated into a system such as the workstation 28. The remote control 114 may include a system to initiate the registration process, acquire the pre-procedure image data, etc.

The network 112 is in communication with a network interface 116. The network interface 116 allows communication from the registration controller 20 to the network 112 and ultimately to other components such as the workstation 28 or various other devices. The network interface 116 allows the network 112 to communicate in remote locations other than the operating room in which the navigation device 10 is located.

The registration controller 20 may also be communication with the registration device 18, the display device 36 and the audible device 37. The display device 36 and the audible device 37, in this example, are part of the workstation. However, separate display devices and audible devices may be provided especially when the registration controller 20 is located away from the workstation 28.

The registration controller 20 may be microprocessor-based and programmed to perform various functions. The blocks provided within the registration controller may be separate processors or modules programmed to perform various functions.

An actuator controller 120 is used to control actuators of the registration device 18. The registration device 18 may include a physical structure, as discussed herein, that may be moved relative to the subject 14. The actuators may be motors or other systems that move the registration device 18. The actuation controller 120 may move the motors based upon received sensor signals from the registration device 18 and are received at the position sensor input 122. Examples of sensors include position sensors that may be distance sensors that sense the distance from the patient and encoders used to sense the position of the moving actuators. The distance sensors may be infrared distance sensors. The actuator controller 120 and the signals from the position sensors in the registration device 18 received at the position sensor input 122 are provided to a position controller 124. Position controller 124, based on the position sensor input 122, controls actuators at the registration device 18 using the actuator controller 120.

An illumination controller 130 is used to control a light source at the registration device 18.

An image processor 132 receives imaging signals from the registration device 18. The registration device 18 generates image signals from an image sensor as will be described in more detail below. The registration device 18 may acquire or generate registration image signals that may be used to register the patient to the pre-procedure image data.

The registration processor 134 may perform a registration of the image data, such as the pre-procedure image data, to the patient space defined by the patient 14 and physical space relative to the patient 14. As discussed further herein, the registration device 18 may acquire an image, which may also be referred to as a registration image, of at least a portion of the patient 14. A common point or fiducial point between the registration image and the pre-procedure image may be used to perform the registration of the patient space to the image space. A position of the points on the patient may be based upon the determination of a distance between the registration device 18 and the patient 14 when acquiring the registration image to determine a position of the points on the patient in the physical space defined by and relative to the patient 14. The registration process may be similar to that discussed above and include a generation or determination of a translation map between the position of the points determined of the patient 14 and of the similar or same points in the pre-procedure image data.

A user interface 142 coupled to the registration controller 20 is used for providing control signals to the various controllers and modules within the registration controller 20. Examples of the user interface 142 include a keyboard, a mouse or a touch screen.

A timer 144 may also be included within the registration controller 20. The timer 144 may record the time of the images received from the registration device 18. This may allow a correlation of a time of determining a position of the registration device, as discussed herein, for use with determining a position of the patient 14 for the registration process.

Figure 2B:
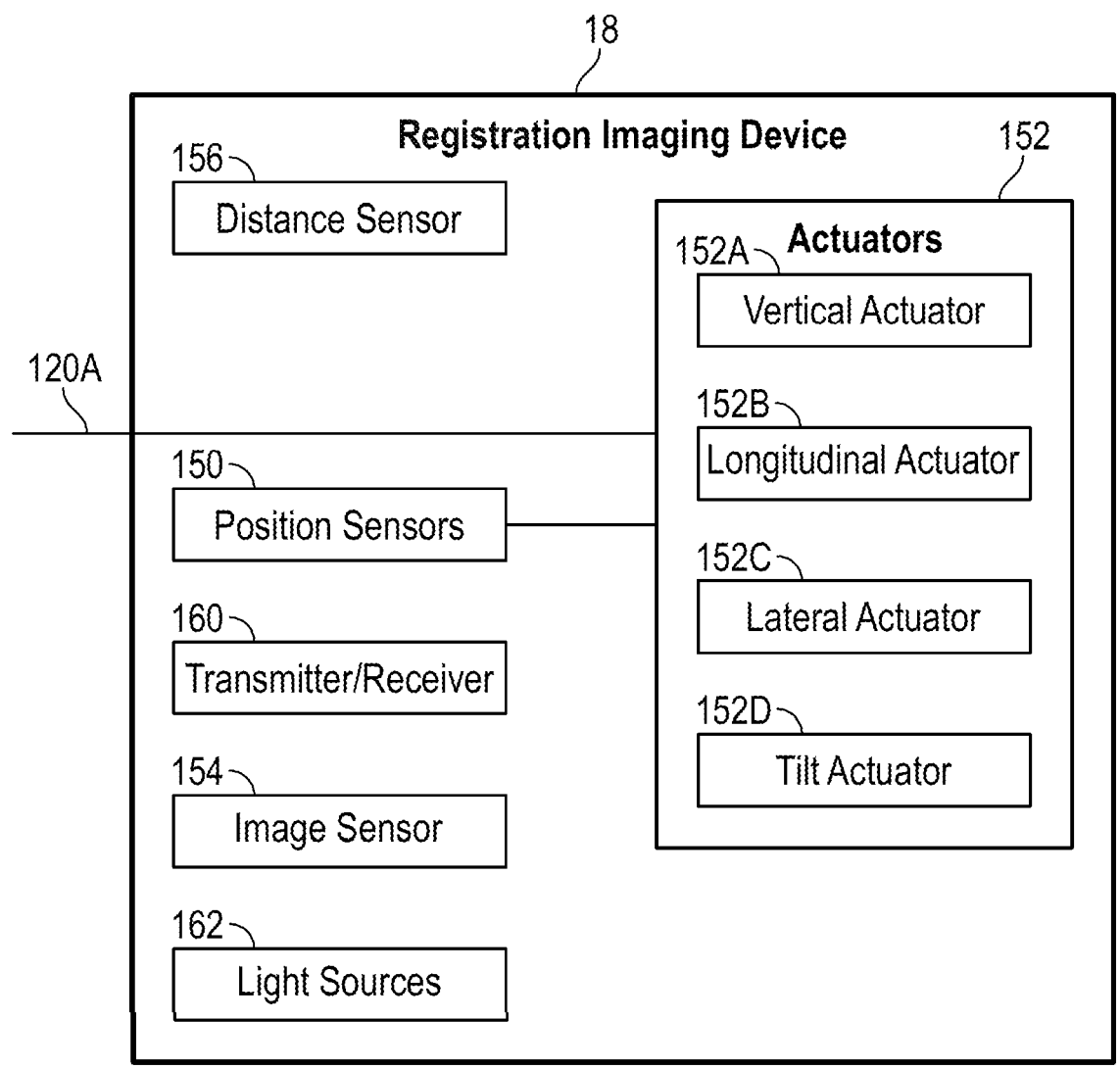
FIG. 2B is a detailed block diagrammatic view of the registration device of FIG. 1.

Referring now to FIG. 2B, the registration device 18 is schematically illustrated in further detail. The registration device 18 may have a plurality of position sensors 150. Each of the actuators and/or arms may have position sensor feedback from a position sensor associated therewith. The position sensors 150 generate a plurality of position signals that are ultimately communicated to the registration controller 20. Control signals from the actuator controller 120 are communicated as signals 120A to the actuators 152. The number and types of actuators 152 may vary depending upon the type of system. In various embodiments, the actuators may include a vertical actuator 152A, a longitudinal actuator 152B, a lateral actuator 152C, and a tilt actuator 152D. The vertical actuator 152A moves an image sensor 154 closer to or away from a patient. The longitudinal actuator 152 moves the image sensor 154 longitudinally relative to the longitudinal axis 22 described above in FIG. 1.

The lateral actuator 152C moves the image sensor 154 laterally or sideways relative to the patient 14. The tilt actuator 152D may tilt the image sensor 154 relative to the patient. In various embodiments, the tilt actuator 152D may allow the image sensor to be placed parallel to the patient and/or the head of the patient.

The actuators 152 may move a selected portion or the entire registration device 18. The actuators 152 may or may not include only the sensors and light sources depending upon the configuration.

A distance sensor 156 may allow the registration device 18 to communicate a distance signal to the registration controller 20 to determine the position and provide feedback relative to the position to the position controller 124. Different types of distance sensors including radar, infrared light time of travel, or laser may be used. Another specific type of distance sensor is a passive infrared (PIR) sensor which may be used to thermally sense the distance of the mask to the patient. A PIR sensor has transmitter and receiver. The transmitter of a PIR sensor may transmit the light (e.g., omnidirectionally), and the receiver receives a reflected IR light off of the patient. Consequently, each PIR sensor determines the distance. Based on the fixture (which acts as a reference), the PIR sensors determine the distance. Various numbers of the passive infrared sensors may be used such as three. The distance sensor 156 calculates the distance to the head and gives the output based on a distance a robotic arm would need to be adjusted to continue the procedure of registration.

A plurality of light sources 160 may be used to illuminate the patient 14 and are controlled by the illumination controller within the registration controller 20. The plurality of light sources 160 may surround the image sensor 154.

The registration device 18 may also include a transmitter/receiver 162. The transmitter/receiver 162 may be referred to as a transceiver 162. The transceiver 162 may be used for communicating signals to and from the registration device 18. The transceiver 162 may, for example, communicate using Bluetooth® wireless communication or another type of wireless technology. The transceiver 162 may also be a wired device. The transceiver 160 communicates with a transceiver 162 located within the registration controller 20. Although direct lines are shown in FIG. 2A between the registration controller 20 and the registration device 18, the transceiver 162 may be used to communicate wirelessly or in wired fashion with the registration device 18.

Figure 2C:
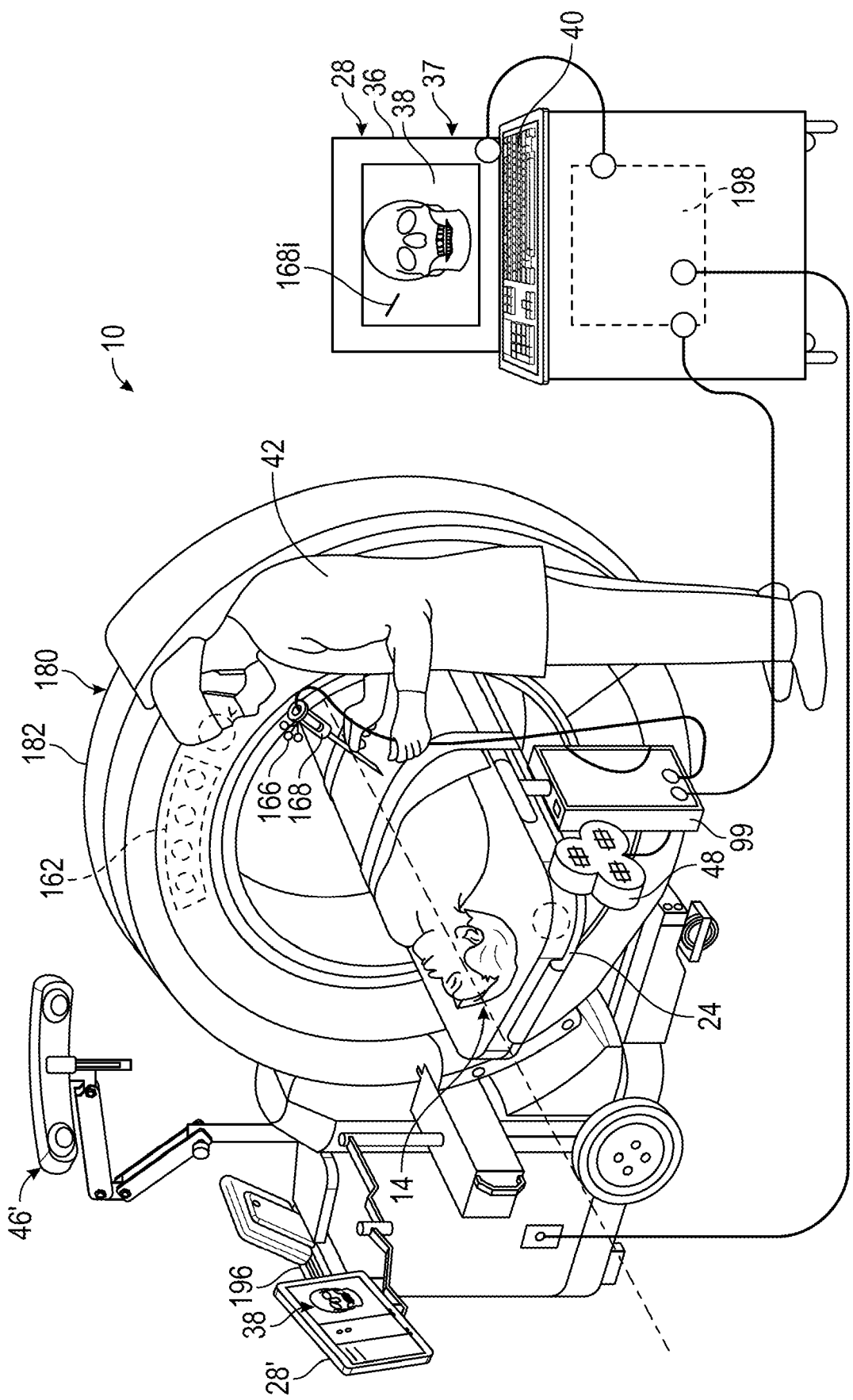
FIG. 2C Is an environmental view of the navigation system with an imaging system.

Referring now to FIG. 2C, a diagrammatic view illustrating an overview of a procedure room or arena is set forth, similar to FIG. 1. The primary difference between FIG. 1 and FIG. 2C is the inclusion of the imaging system 180. Prior to the process above the pre-procedure image may be obtained with any appropriate imaging system, indulging the imaging system 180. In various embodiments, the procedure room may include a surgical suite having the navigation system 10 that can be used relative to the patient or subject 14. The navigation system 10 can be used to track the location of one or more tracking devices, tracking devices may include an imaging system tracking device 162 to track the imaging system 180. Also, a tool tracking device 166 similar or identical to the tracking device 34a may be included on a tool 168 similar to identical to the device 12. The tool 12, 168 may be any appropriate tool such as a drill, forceps, catheter, speculum or other tool operated by the user 42. The tool 168 may also include an implant, such as a stent, a spinal implant or orthopedic implant. It should further be noted that the navigation system 10 may be used to navigate any type of instrument, implant, stent or delivery system, including: guide wires, arthroscopic systems, orthopedic implants, spinal implants, deep brain stimulation (DBS) probes, etc. Moreover, the instruments may be used to navigate or map any region of the body. The navigation system 10 and the various instruments may be used in any appropriate procedure, such as one that is generally minimally invasive or an open procedure including cranial procedures.

The imaging device 180 may be used to acquire pre-, intra-, or post-operative or real-time image data of a subject, such as the subject 14. It will be understood, however, that any appropriate subject can be imaged and any appropriate procedure may be performed relative to the subject. In the example shown, the imaging device 180 comprises an O-Arm® imaging device sold by Medtronic Navigation, Inc. having a place of business in Louisville, Colorado, USA. The imaging device 180 may have a generally annular gantry housing 182 in which an image capturing portion is moveably placed. The image capturing portion may include an x-ray source or emission portion and an x-ray receiving or image receiving portion located generally or as practically possible 180 degrees from each other and mounted on a rotor relative to a track or rail. The image capturing portion can be operable to rotate 360 degrees during image acquisition. The image capturing portion may rotate around a central point or axis, allowing image data of the subject 14 to be acquired from multiple directions or in multiple planes. The imaging device 180 can include those disclosed in U.S. Pat. Nos. 7,188,998; 7,108,421; 7,106,825; 7,001,045; and 6,940,941; all of which are incorporated herein by reference, or any appropriate portions thereof. In one example, the imaging device 180 can utilize flat plate technology having a 1,720 by 1,024 pixel viewing area.

The position of the imaging device 180, and/or portions therein such as the image capturing portion, can be precisely known relative to any other portion of the imaging device 180. The imaging device 180, according to various embodiments, can know and recall precise coordinates relative to a fixed or selected coordinate system. This can allow the imaging system 180 to know its position relative to the patient 14 or other references. In addition, as discussed herein, the precise knowledge of the position of the image capturing portion can be used in conjunction with a tracking system to determine the position of the image capturing portion and the image data relative to the tracked subject, such as the patient 14.

The imaging device 180 can also be tracked with the tracking device 162. The image data defining an image space acquired of the patient 14 can, according to various embodiments, be inherently or automatically registered relative to an object space. The object or patient space can be the space defined by a patient 14 in the navigation system 10. The automatic registration can be achieved by including the tracking device 162 on the imaging device 180 and/or the determinable precise location of the image capturing portion. According to various embodiments, as discussed herein, imagable portions, virtual fiducial points and other features can also be used to allow for registration, automatic or otherwise. It will be understood, however, that image data can be acquired of any subject which will define the patient or subject space. Patient space is an exemplary subject space. Registration allows for a translation between patient space and image space.

The patient 14 may be fixed within navigation space defined by the navigation system 10 to allow for or maintain registration and/or the registration device 18 may be used to obtain and/or maintain registration. As discussed further herein, registration of the image space to the patient space or subject space allows for navigation of the instrument 12, 168 with reference to the image data. When navigating the instrument 168, a position of the instrument 168 can be illustrated relative to image data acquired of the patient 14 on the display device 36, such as superimposed as a graphical representation (e.g., icon) representing the tool 12, 168 in a selected manner, such as mimicking the tool 12, 168. Various tracking systems, such as one including the optical localizer 46' or the electromagnetic (EM) localizer 48 can be used to track the instrument 168.

As discussed above, more than one tracking system can be used to track the instrument 168 in the navigation system 10. According to various embodiments, these can include an electromagnetic tracking (EM) system having the EM localizer 48 and/or an optical tracking system having the optical localizer 188. Either or both of the tracking systems can be used to track selected tracking devices, as discussed herein. It will be understood, unless discussed otherwise, that a tracking device can be a portion trackable with a selected tracking system. A tracking device need not refer to the entire member or structure to which the tracking device is affixed or associated.

It is further appreciated that the imaging device 180 may be an imaging device other than the O-Arm® imaging device and may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging devices can also include MRI, CT, ultrasound, etc.

In various embodiments, an imaging device controller 196 may control the imaging device 80 and can receive the image data generated at the image capturing portion and store the images for later use. The controller 196 can also control the rotation of the image capturing portion of the imaging device 180. It will be understood that the controller 196 need not be integral with the gantry housing 182 but may be separate therefrom. For example, the controller 196 may be a portion of the navigation system 10 that may include a processing and/or control system including a processing unit or processing system 198. The controller 196, however, may be integral with the gantry housing 182 and may include a second and separate processor, such as that in a portable computer.

The patient 14 can be fixed onto the operating table 24. According to one example, the table 104 can be an Axis Jackson® operating table sold by OSI, a subsidiary of Mizuho Ikakogyo Co., Ltd., having a place of business in Tokyo, Japan or Mizuho Orthopedic Systems, Inc. having a place of business in California, USA. Patient positioning devices can be used with the table and include a Mayfield® clamp or those set forth in commonly assigned U.S. patent application Ser. No. 10/405,068 entitled "An Integrated Electromagnetic Navigation And Patient Positioning Device", filed Apr. 1, 2003 which is hereby incorporated by reference.

The position of the patient 14 relative to the imaging device 80 can be determined by the navigation system 10. The tracking device 162 can be used to track and locate at least a portion of the imaging device 180, for example the gantry housing 182. The patient 14 can be tracked with the dynamic reference frame 44, as discussed in FIG. 1, which may be invasive and/or not invasive or minimally invasive. That is, a patient tracking device or dynamic reference device 44 may be used to receive or generate signals that are communicated to an interface portion 99.

Accordingly, the position of the patient 14 relative to the imaging device 180 and relative to the registration device 18 of FIG. 1 can be determined initially and when movement, such as skull movement is detected. Further, the location of the imaging portion can be determined relative to the housing 182 due to its precise position on the rail within the housing 182, substantially inflexible rotor, etc. The imaging device 180 can include an accuracy of within 10 microns, for example, if the imaging device 180 is an O-Arm® imaging device sold by Medtronic Navigation, Inc. having a place of business in Louisville, Colorado. Precise positioning of the imaging portion is further described in U.S. Pat. Nos. 7,188,998; 7,108,421; 7,106,825; 7,001,045; and 6,940,941; all of which are incorporated herein by reference.

According to various embodiments, the imaging device 180 can generate and/or emit x-rays from the x-ray source that propagate through the patient 14 and are received by the x-ray imaging receiving portion. The image capturing portion generates image data representing the intensities of the received x-rays. Typically, the image capturing portion can include an image intensifier that first converts the x-rays to visible light and a camera (e.g. a charge couple device) that converts the visible light into digital image data. The image capturing portion may also be a digital device that converts x-rays directly to digital image data for forming images, thus potentially avoiding distortion introduced by first converting to visible light.

Two dimensional and/or three-dimensional fluoroscopic image data that may be taken by the imaging device 180 can be captured and stored in the imaging device controller 196. Multiple image data taken by the imaging device 180 may also be captured and assembled to provide a larger view or image of a whole region of a patient 14, as opposed to being directed to only a portion of a region of the patient 14. For example, multiple image data of the patient's 14 spine may be appended together to provide a full view or complete set of image data of the spine.

The image data can then be forwarded from the image device controller 196 to the navigation computer and/or processor system 198 that can be a part of a controller or workstation 28. It will also be understood that the image data is not necessarily first retained in the controller 196, but may also be directly transmitted to the workstation 28. The workstation 28 can provide facilities for displaying the image data as an image 38 on the display 36, saving, digitally manipulating, or printing a hard copy image of the received image data. The user interface 40 allows the user 42 to provide inputs to control the imaging device 180, via the image device controller 96, or adjust the display settings of the display 36. The workstation 28 may also direct the image device controller 196 to adjust the image capturing portion of the imaging device 180 to obtain various two-dimensional images along different planes in order to generate representative two-dimensional and three-dimensional image data.

With continuing reference to FIG. 1, the navigation system 10 can further include the tracking system including either or both of the electromagnetic (EM) localizer 94 and/or the optical localizer 188. The tracking systems may include a controller and interface portion 99. The interface portion 99 can be connected to the processor system 198, which can include a processor included within a computer. The EM tracking system may include the STEALTHSTATION® AXIEM™ Navigation System, sold by Medtronic Navigation, Inc. having a place of business in Louisville, Colorado; or can be the EM tracking system described in U.S. Pat. No. 7,751,865 issued Jul. 6, 2010, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the navigation system 10 may also be or include any appropriate tracking system, including a STEALTHSTATION® TREON® or S7™ tracking systems having an optical localizer, that may be used as the optical localizer 188, and sold by Medtronic Navigation, Inc. of Louisville, Colorado. Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems 48, 46', imaging device 180, etc. Alternatively, various portions, such as the instrument 168 may employ a wireless communications channel, such as that disclosed in U.S. Pat. No. 6,474,341, entitled "Surgical Communication Power System," issued Nov. 5, 2002, herein incorporated by reference, as opposed to being coupled directly to the processor system 198. Also, the tracking devices 162, 166 can generate a field and/or signal that is sensed by the tracking system(s) 48, 46'.

Various portions of the navigation system 10, such as the instrument 168, and others as will be described in detail below, can be equipped with at least one, and generally multiple, of the tracking devices 166. The instrument can also include more than one type or modality of tracking device 166, such as an EM tracking device and/or an optical tracking device. The instrument 68 can include a graspable or manipulable portion at a proximal end and the tracking devices may be fixed near the manipulable portion of the instrument 68.

Additional representative or alternative localization and tracking system is set forth in U.S. Pat. No. 5,983,126, entitled "Catheter Location System and Method," issued Nov. 9, 1999, which is hereby incorporated by reference. The navigation system 10 may be a hybrid system that includes components from various tracking systems.

According to various embodiments, the navigation system 10 can be used to track the instrument 168 relative to the patient 14. The instrument 168 can be tracked with the tracking system, as discussed above. Image data of the patient 14, or an appropriate subject, can be used to assist the user 42 in guiding the instrument 168. The image data, however, is registered to the patient 14. The image data defines an image space that is registered to the patient space defined by the patient 14. The registration can be performed as discussed herein, automatically, manually, or combinations thereof.

Briefly, registration allows a translation map to be generated that allows for the physical location of the instrument 168 to be displayed relative to the image space of the image data. The translation map allows the tracked position of the instrument 168 to be displayed on the display device 36 relative to the image data 38. The graphical representation 168i, also referred to as an icon, can be used to illustrate the location of the instrument 168 relative to the image data 38.

The image data 38 of the subject 14, which may be pre-procedure image data that may be acquired with any appropriate imaging system including the imaging system 180 may be displayed on the display device. As noted above, the image 38 may include an illustration of any appropriate portion of the subject, such as a head or skull of the subject. The image data 38 defining an image space may need to be registered to the subject space or physical space defined relative to the patient 14 to allow for tracking of the instrument 12, 168 relative to the patient 14 and allow its representation to be displayed relative to the image 38. The registration may be performed within the registration system 16 as illustrated in FIG. 1 and further with reference to FIGS. 3A-3D and according to a method 340 as illustrated in FIG. 3E.

Figures 3A, 3B:
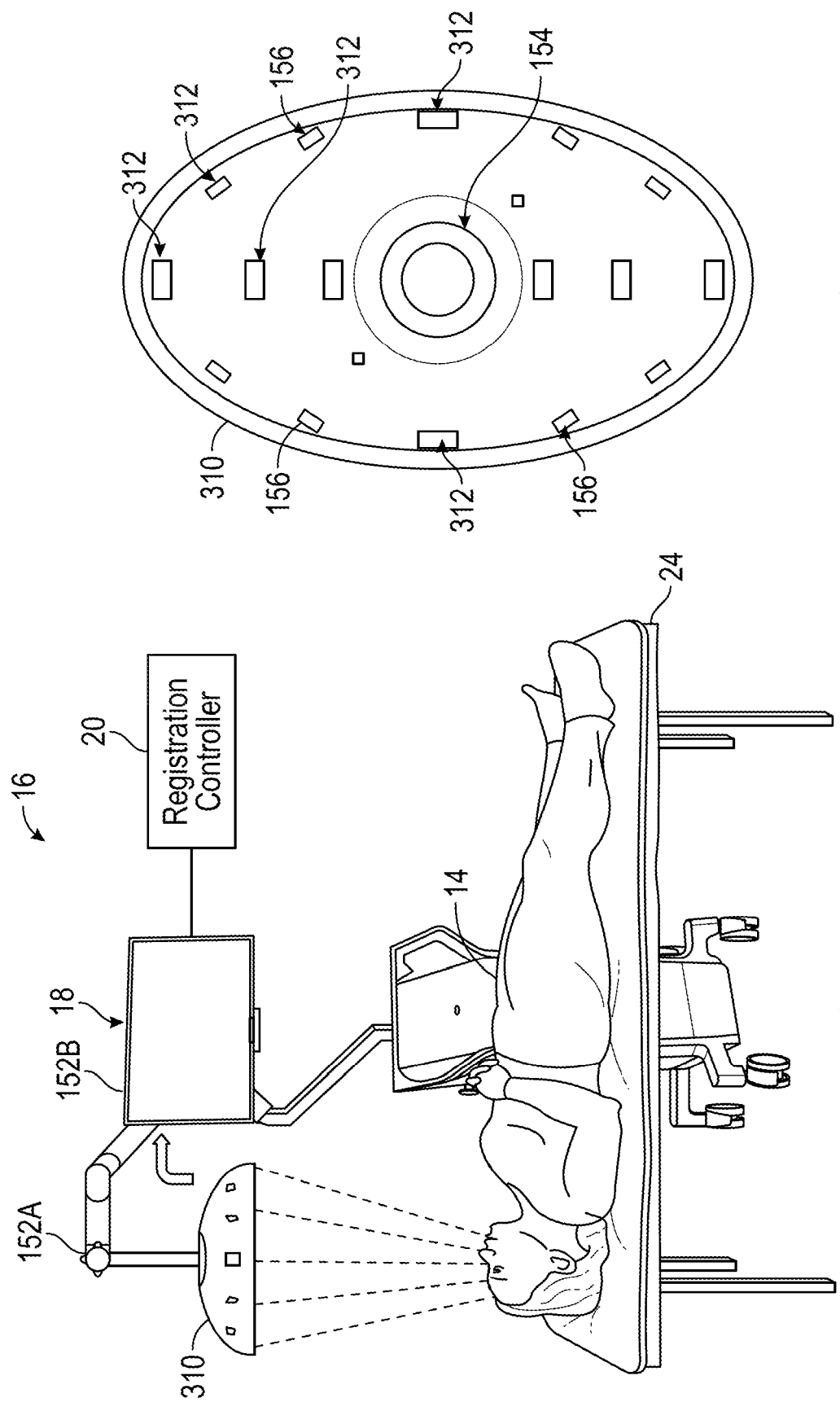
FIG. 3A is a diagrammatic view of one specific example of a registration system.
FIG. 3B is a diagrammatic view of a mask of the registration system of FIG. 3A.

Referring now to FIG. 3A, the registration controller 20 relative to the registration device 18 is set forth. The registration device 18, as mentioned above, may have a plurality of actuators of which exemplary the vertical actuator 152A and the longitudinal actuator 152B are provided. In this example, the registration device 18 is fixedly coupled to a portion of the operating table 24. A carrying portion, also referred to as a mask 310, may be positioned over the patient 14 using the actuators 152.

Referring now also to FIG. 3B, the mask 310 may have a plurality of distance sensors 312. The distance sensors 312 may be infrared (also referred to as infra-thermal) sensors. The distance sensors 312 may be positioned around the image sensor 154. The distance sensors 312 may be at known and fixed positions relative to the image sensor 154 so that any distance determined with the distance sensors 312 may be correlated to the image sensor 154 and an image acquired with the image sensor. The infrared sensors 312 may act as distance sensors to sense the distance from the patient. As mentioned above. Passive infrared (PIR) sensors are one suitable example of the distance sensor. The PIR may emit and/or receive infrared energy to determine a distance to a surface from the PIR. The position of the PIR sensor relative to the image sensor 154 may be known and used to determine the position of the image sensor relative to the patient 14.

The image sensor 154 may be a camera of any appropriate type. The camera may include a selected digital capture sensors such as a Complementary metal-oxide-semiconductor (CMOS) and/or a charged couple device (CCD). A plurality of light sources 160, which may include LED lights, may also be positioned around the image sensor 154 to illuminate the patient 14. The illumination may assist in acquiring high quality image data of the patient 14. The mask 310 may be formed of a medical grade material such as polycarbonate. In this example, the mask 310 is an elongated oval corresponding generally to a typical elongated head of a human that may be the patient 14.

Figure 3D:
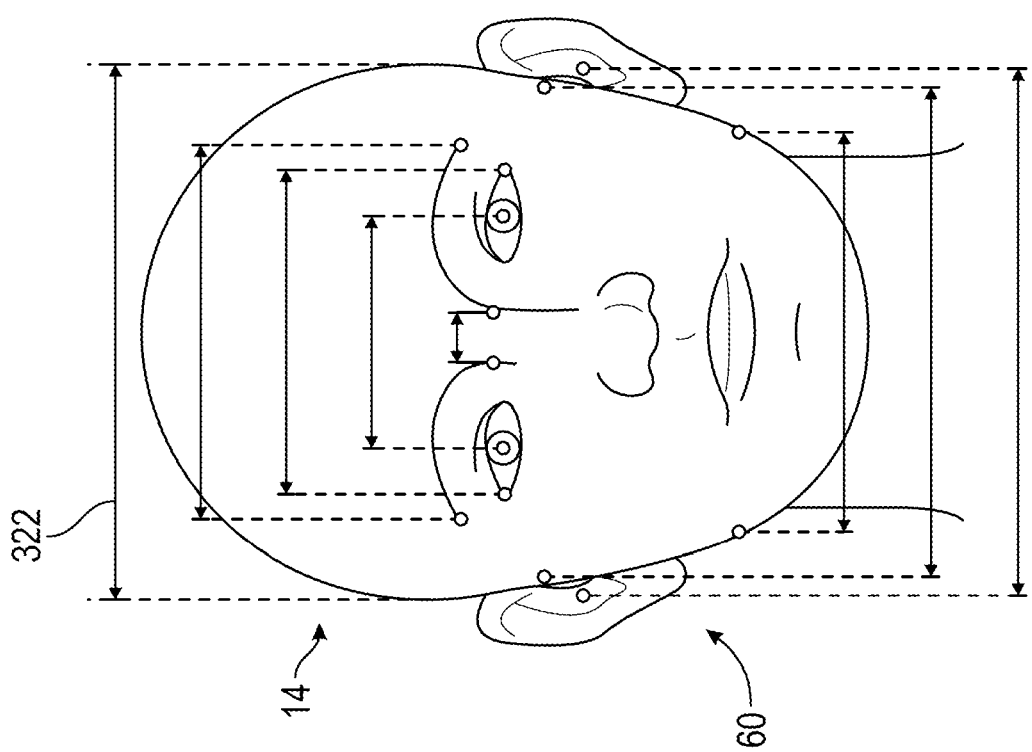
FIGS. 3C and 3D are facial images having points and measurements thereon.
Figure 3C:
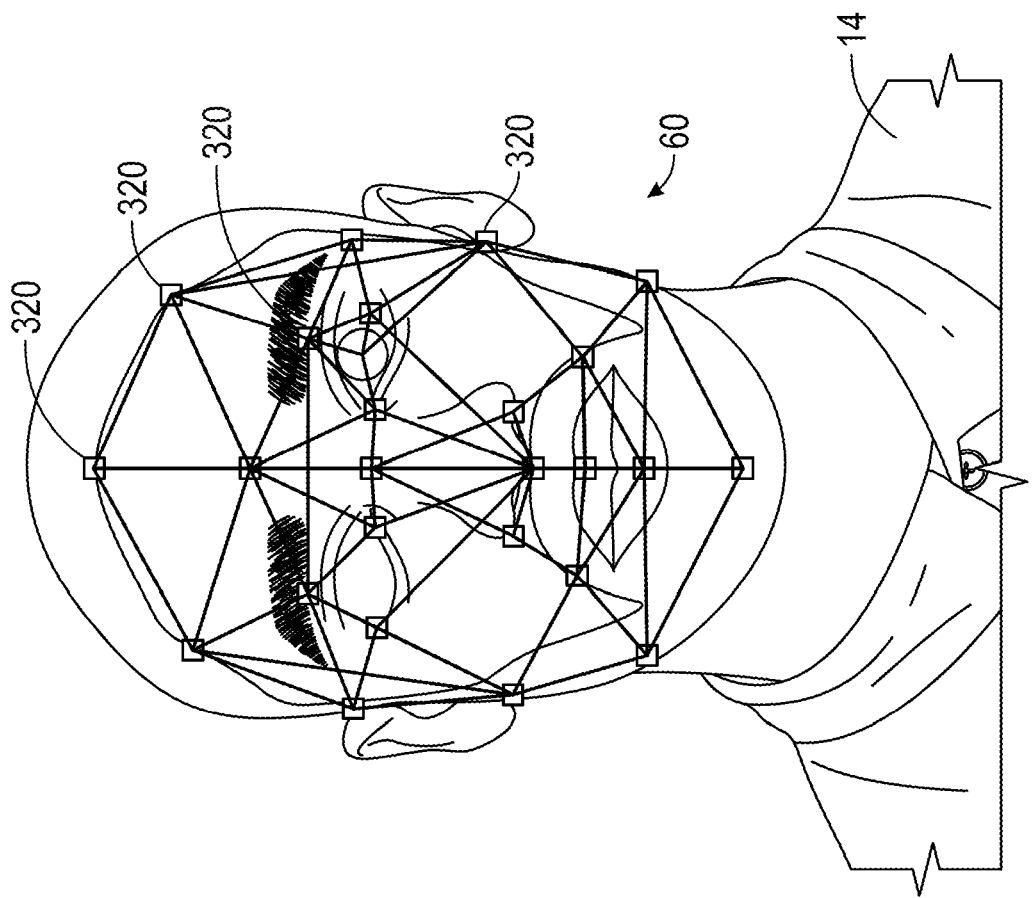
Figure 3E:
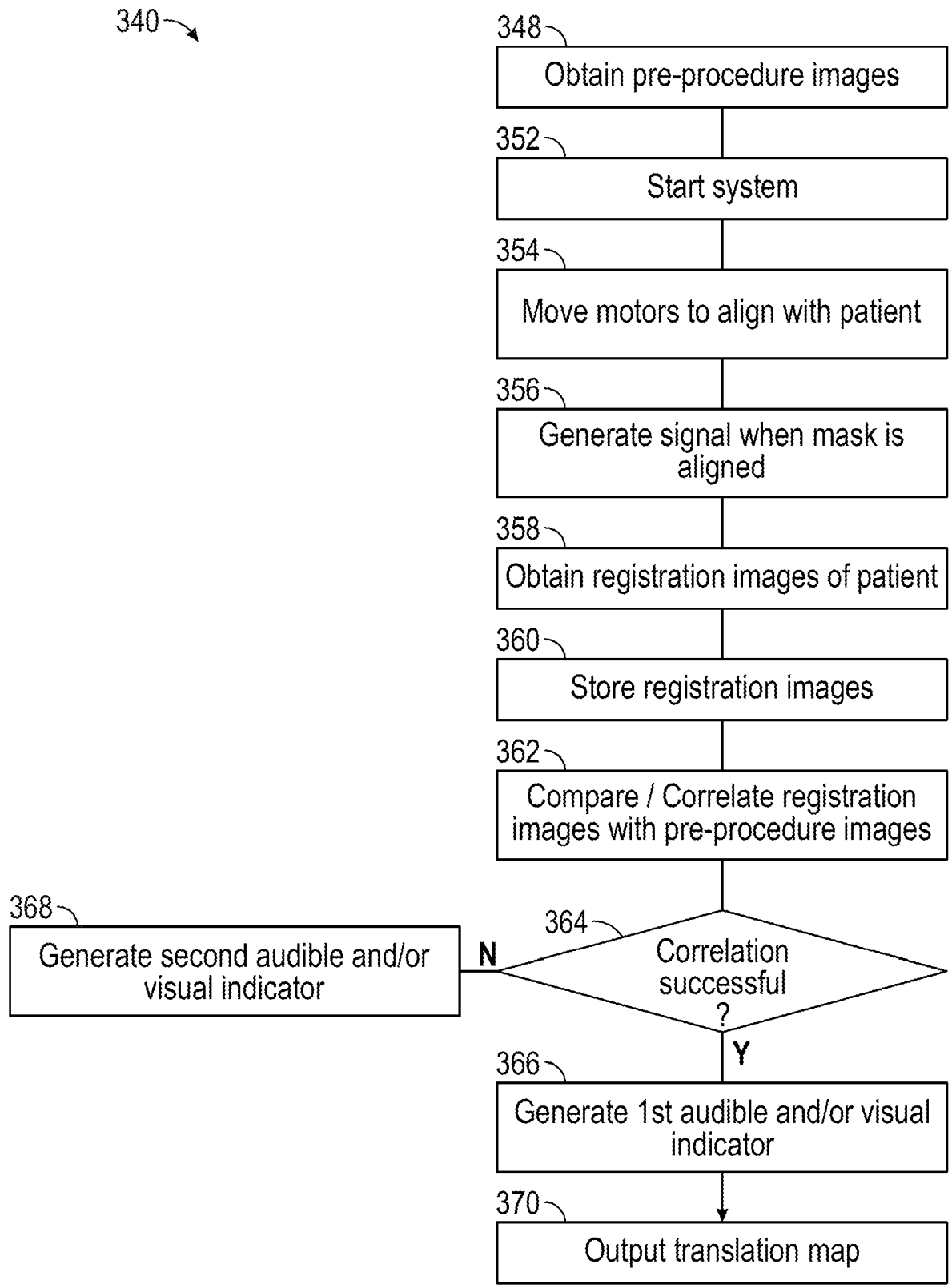
FIG. 3E is a flowchart of a method of operating the system of FIG. 3A.

Referring now to FIGS. 3C and 3D, registration features such as various points 320 may be identified in an image on the patient 14. The features or points 320 may include such anthropometric locations such as the edges of the eyes, the position of the ear lobes, chin, mouth, nose and various other locations. In FIG. 3D, measurements 322 may be used for comparison with measurements in the pre-procedure image data, such as received from the image system 180. The points 320, the distances 322, and/or the distance of the imagining device 154 from the patient 14 may be used to determine a registration. As discussed above, the points in the pre-acquired image may be compared to the points 320, the distances 322, and/or the distance of the imagining device 154 to make a registration.

Based on the position of the points or the measurements or both, the comparison module 136 may generate a signal indicative of whether or not a registration is possible and/or is made between the patient space and the image space. During a procedure, the user 42 may block a portion of points or measurements from view of the camera or image sensor 154. For example, a certain number of points may be identified in the pre-acquired image data and the same or all of the points may be identified on the patient 14 in the registered image data from the imaging device 154. In some configurations, only about 80% of the points 320 or measurements 322 are needed to determine registration. That is, when the user 42 blocks a predetermined number of points, the other points may be used to determine registration. The points in the image and their physical position relative to eh patient 14 in patient space are determined by a distance by the distance sensor 156. Further, the position relative to the patient 14 may be further determined relative to the patient 14 due to movement of the motors associated with the actuators 152 may be moved by electric signals that allow the position controller 124 of FIG. 2A to control the precise position needed. For example, the motor may be rotated a predetermined number of rotations based upon feedback provided by a position signal from the position sensors 150 which may be a potentiometer, an encoder, or part of the motor as a servo motor.

Referring now to FIG. 3E, a method 340 is illustrated in a flow chart of the system illustrated in FIGS. 3A-3D. In block 348, a pre-procedure image is obtained using one of the systems described above. The image data obtained in block 348 may have one or more points, as discussed above, and may be determined therein. In block 352 the registration system 18 that may be initiated, for example by a user interface to start the system. The user interface may be a remote control from which signals are communicated through the network 112 illustrated in FIG. 2A. However, a direct wire or wireless communication may be used to initiate operation of the system through the registration controller 20 through the user interface 142 and/or the workstation 28.

In block 354, the mask may be posited, such as selectively aligned, with a portion of the patient. In various embodiments, the motors of the actuators are moved to move the mask and the mask may be aligned with a face of the patient 14. In block 356, a signal is generated when the mask is aligned with the patient. For example, a tone may be generated by the audible device 37. At the same time, a visual display indicator on the display 36 may also provide an indication of alignment of the mask with the face of the patient 14.

In block 358, registration images or data of the patient are obtained. For example, certain landmark features such as the position of bones, physical features (e.g., corner of an eye), and distances between physical features (e.g., distance between two corners of two eyes) are obtained. Facial features and their relationships are illustrated in FIGS. 3C and 3D. In block 360, the registration images may be stored in the memory 138.

A comparison is made in block 362 between registration data corresponding the registration features, such as the registration distances in the registration images, and the same features in the pre-procedure images. The comparison determines whether the registration features of the images correlate and a registration of the patient space of the patient 14 and the image space is possible and/or has occurred. When correlation is successful, in block 364, block 366 generates an audible and/or visual indicator by way of the display device 36 or the audible device 37 to indicate or provide an indication to the user 42 that correlation has been successful. The correlation may be used to generate the translation map, as discussed above, to allow a registration of the patient space to the image space. This registration may be output in block 370. In block 364, when the correlation is unsuccessful, a second audible and/or visual indicator 368 may be used to indicate to the user 42 that the correlation is not successful. This may result in corrective measures such as moving the patient or the registration device 18 to acquire a second registration image. The error of the procedure may be checked and if the error is not within the defined threshold, re-registration may be performed. After an initial registration, the system may check for the error such as a different is distance of the registration device form the patient. If the device is not within a defined threshold there may be or be required a re-registration. The number of data points may also be adjusted upward as well to improve registration accuracy.

And to improve accuracy we are increasing the intake of more data points. The system illustrated in FIGS. 3A-3E allows complete replacement of manual registration with the automatic registration described herein. That is, the registration except for the initiation process may be automated. An elevated level of accuracy of registration may be obtained. In one exemplary embodiment, the registration may take about 30 seconds which is significantly faster than a manual process. The system may allow the registration to be performed automatically, is easily controlled remotely, and preventive maintenance is relatively easy on such systems.

Figure 4A:
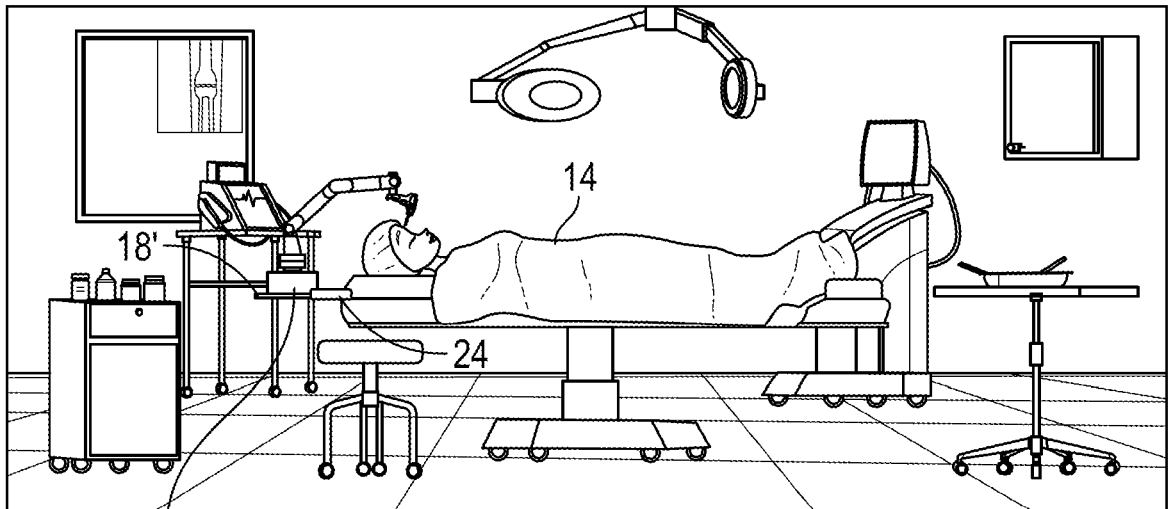
FIG. 4A is a second example of a registration system.

Referring now to FIG. 4A, a registration device 18' is illustrated as a mechanically adjustable arm 408 coupled to the operating table 24 near a head end thereof. Thus, as the operating table 24 moves, the registration device 18' also moves. The registration device 18' may be similar to the registration device 18 noted above, save for the differences noted herein.

Figure 4B:
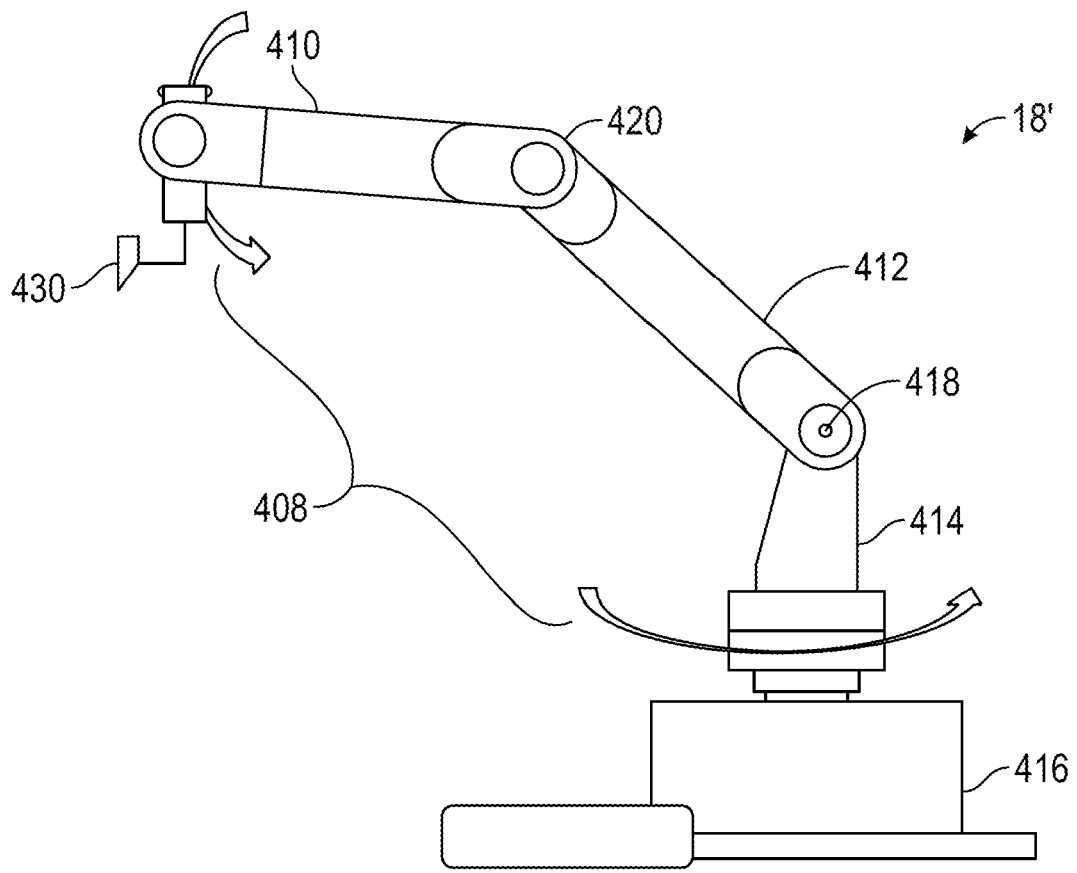
FIG. 4B is a diagrammatic view of a mechanical arm of the system of FIG. 4A.

Referring now also to FIG. 4B, the registration device 18' is illustrated in further detail. In this example, the actuators of the mechanically adjustable arm 408 are incorporated into various portions thereof including a wrist portion 410, a forearm portion 412, and a shoulder portion 414. A base 416 is mounted relative to the bed or operating table 24. For example, the base may be fixed to the operating table 24. The shoulder portion 414 may move, e.g., around, a vertical axis defined relative to the base 416. The forearm 412 may move, e.g., rotate, relative to an axis 420. Likewise, the wrist portion 410 may also move, e.g., rotate, relative to the forearm 412. The robotic arm may be used to move a scanner 430 that may be used to linearly scan at least a portion, such as the face, of the patient 14. The wrist portion 410, the forearm portion 412, and the shoulder portion 414 move the scanner 430 in selected degrees of freedom, such as six degrees of freedom (i.e., directions). That is, the vertical, lateral, and longitudinal directions all have both positive and negative directions. Therefore, the wrist portion 410, the forearm portion 412 and the shoulder portion 414 are a vertical actuator, a lateral actuator and a longitudinal actuator. Further, each of the portions may rotate relative to one another. It should be noted that feedback may be provided to the registration controller 20. Feedback may include the position of one or more of the actuators and/or when one or more of the actuators is not in the proper position. Therefore, feedback may be provided to the user 42 audibly, visibly, or both when an improper position is present.

Figure 4C:
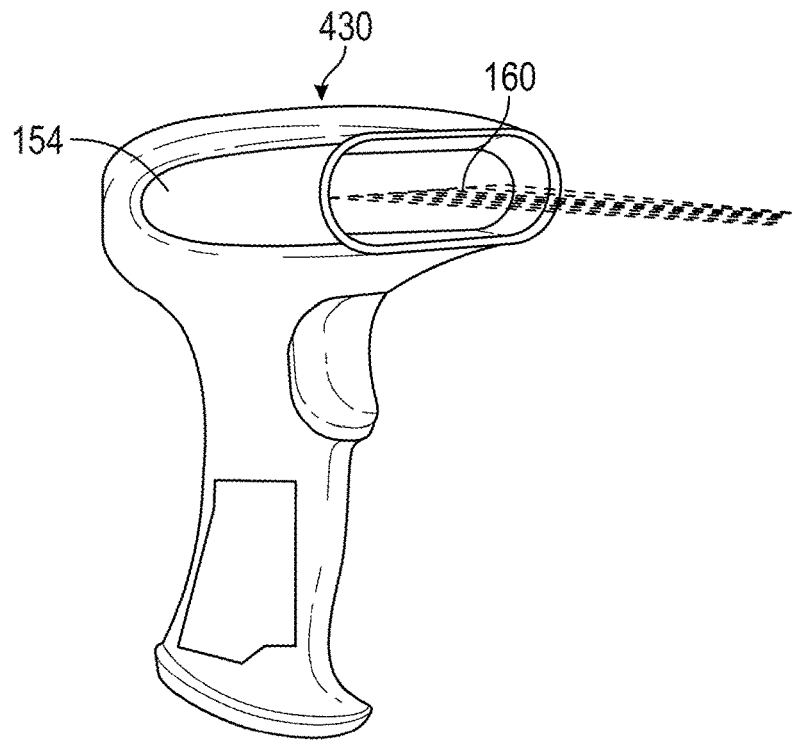
FIG. 4C is a diagrammatic view of a scanner coupled to the arm of FIG. 4B.

Referring now to FIG. 4C, the facial scanner 430 is illustrated in further detail. The scanner 430 includes one or more light sources 160 and the image sensor 154 which may be similar to that as described above in FIG. 2B. The image scanner 154, according to various embodiments, may be a light detector that detects any selected wavelength of light. For example, the image sensor 154 may be a charge coupled device (CCD). and/or a Complementary metal-oxide-semiconductor (CMOS). The image sensor 154 may have a selected field of view that may differ based on a selected application, as discussed herein.

Figure 4D:
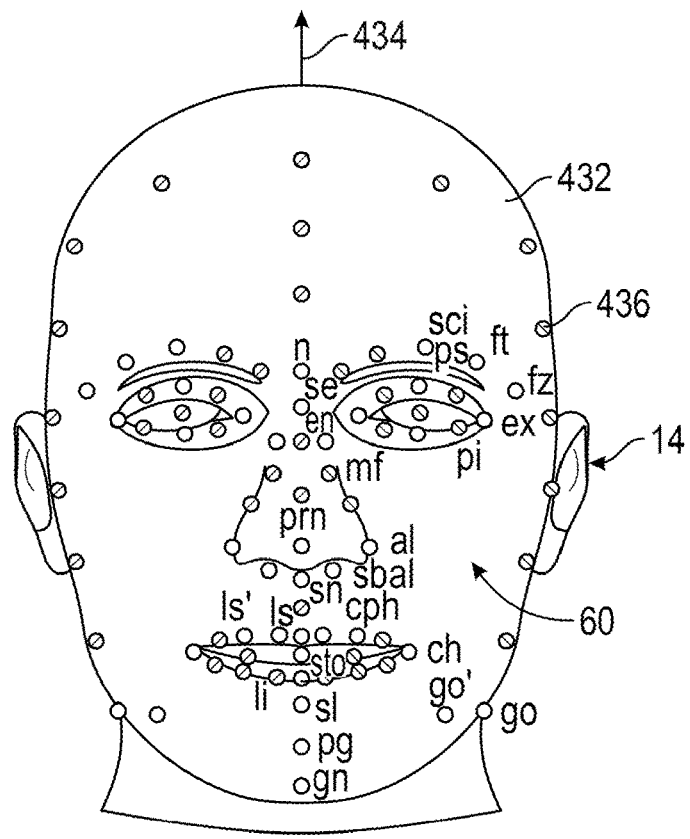
FIG. 4D is a representation of the anthropometric points determined by the scanning process.

The scan may take place by scanning the face 432 of the patient that includes one or more data points 436 as illustrated in FIG. 4D by moving the scanner 430 relative to the face, such as in a longitudinal direction illustrated by axis 434. In FIG. 4D, specific points 436 are recorded by the scanned image. Ultimately, the data points and/or the scanned image is provided to the comparison module 136 where it is compared to the pre-procedure image provided by the pre-procedure image system 110 illustrated above. The scanner 430 and the light sources 160 may use any appropriate wavelength and one or more wavelengths, such as infrared light, visible light, or both, to obtain the positions of anthropometric points that are unique to each patient 14, such as the patient face. In one example, the points 436 are determined from the top to the bottom of the head of the patient 14. Scanning may take place in less than 10 seconds and work at a distance of about one meter.

Figure 4E:
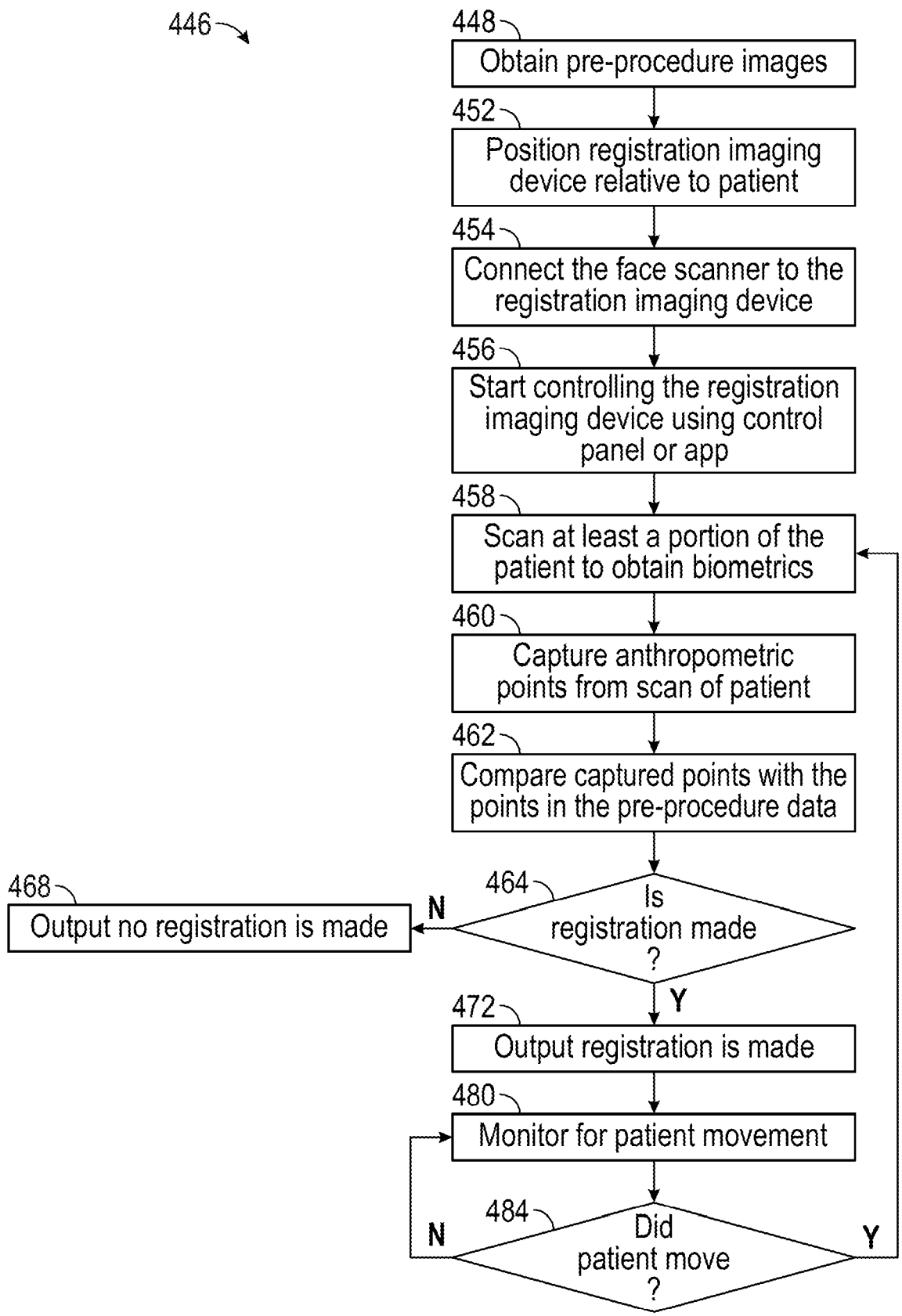
FIG. 4E is a flowchart of a method for operating the system of FIG. 4A.

Referring now to FIG. 4E, a method 446 is illustrated for registration process with the scanner 430. The process 446 may begin in block 458 where pre-procedure images or data of the patient are obtained. In the pre-procedure image data one or more fiducial points for registration may be identified. For example, certain landmark features such as the position of bones, physical features, and distances between physical features are obtained. The registration device 18' may be positioned relative to the subject 14, such as mounted on the bed or operating table of the patient in block 452.

In block 454, the facial scanner 430 may be, optionally, fixed to the registration device 18'. That is, the scanner 430 may be placed relative to the subject 14 and/or connected to the arm 408. The scanner 430 may be placed, however, at any appropriate time. Further, the registration device 18' may include the scanner 430 provided permanently with the arm 408.

In block 456, the registration device is started using a control panel or application within the workstation 28. The application or app may also be located at a remote location and has a user interface that acts as the control panel. An automatic process for registration may be initiated.

In block 458, the scanner 430 scans a selected portion of the patient 14, such as at portion or the entire face of the patient to obtain data regarding the patient 14, such as the biometrics of the patient. The biometrics may include the facial features corresponding to the points 436 illustrated in FIG. 4D. In block 460, the anthropometric points 436 on the face may be captured as illustrated in FIG. 4D. In various embodiments, the image processor 132 may receive the entire image from the scanner 430 which may then be reduced to the points illustrated in FIG. 4D. In various embodiments, if selected, the reduction of the image to the data points 436, which may be anthropometric points, is performed at block 460. The scanner 430 scans using an infrared light (e.g., beam, such as a laser beam) and infrared dots may be determined on the subject and the dots are the anthropometric points 436 which are unique to each face.

In block 462, the captured data points are compared to the data points on images received from the pre-procedure image system. The images from the pre-procedure image system may be 3D images. The comparison of the points in the captured registration image with the registration device may be made to the pre-procedure image data, as discussed above. The identification of the anthropometric points 436 in the registration image data may be compared to the same or similar points in the pre-procedure image data. Therefore, the comparison in block 462 may allow for a comparison between the registration image data (which defines and/or is defined by the subject space that is physical space) and the pre-procedure image data to determine a registration therebetween and create a translation map for the registration.

The process 446 may then proceed to determining whether a registration is made in block 464. As discussed above, a determination of whether the registration is made due to the comparison in block 462 may be made in block 464. An indication may be made to the user 42 regarding the registration success. For example, if no registration is made or a determination that registration is not made a No path may be followed and an output of No registration is made may be output in block 468. The output may be any appropriate output, such as those discussed above. The output or indicator may be audible, visible, or in the appropriate indicator.

If a registration is made a Yes path may be followed and an output that registration is made may be indicated in block 472. Again the indication may be any appropriate indicator such as a visible indicator, a sound indicator, or the like. Generally, the indicator output of block 468 may differ from the indicator output in block 472. Thus, the user 42 may be made aware of the success of the registration.

In addition, the process 446 may allow for maintaining a registration or for automatic re-registering the patient 14 if the patient moves during the procedure. The registration may be made due to the comparison in block 462. However, if the patient 14 moves, e.g., skull movement, the patient space or subject space may move and no longer be registered to the image space. Thus, monitoring the movement of the patient may be performed in block 480. The monitoring for the movement of the patient may be made substantially automatically such as by continually scanning, or scanning at a selected rate, the subject 14 with the scanner 430. In various embodiments, however, the monitoring for patient movement in block 480 may also be made manually, such as by the use of 42.

A determination of whether the patient has moved may be made in block 484. The determination of whether the patient has moved may be made based upon determining a threshold of movement of the patient 14. For example, the scanner 430 may determine that one or more of the points 436 moved an amount greater than a threshold, such as greater than 1 mm.

If a determination that the patient has not moved, a No path may be followed to return to block 480 to continue monitoring for movement of the patient. If a patient's movement has been determined in block 484, a Yes path may be followed to block 458 to again scan the patient 14 to obtain biometric points and perform the registration as illustrated in the method 446.

Therefore, the method 446 may not only register the subject 14 to the image space in a first instance, the system and method may also monitor the patient for movement to perform a substantially automatic re-registration if selected. If the re-registration is occurring an indication may also be made to the user 42 that a re-registration is occurring and/or is required so that the user 42 may understand that the illustrated tracked position of the instrument 12, 168 may not be accurate and the procedure may be paused. Nevertheless, the method 446 may allow for registration of the subject space defined by the subject patient 14 to the image space defined by the image, such as acquired with the preoperative or pre-procedure image.

The system and method illustrated in FIGS. 4A-4D allow the placement of manual registrations and allows an automatic and continuous highly accurate registration, which may be compared to manual registrations. The entire automated registration may take about 20 to 30 seconds. Because the device may be remote control, the system may be actuated from anywhere in the world.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C #, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system comprising:
a registration device comprising a plurality of actuators, the plurality of actuators moving an imaging portion of the registration device relative to a patient, said registration device comprising an image sensor of the imaging portion generating a registration image of the patient; and
a controller determining registration data from the registration image and comparing the registration data to a pre-operative image;
wherein comparing the registration data to the pre-operative image is operable to register a physical space to an image space of the pre-operative image;
wherein the registration device comprises a mask coupled to the actuators, said mask comprising a plurality of distance sensors and a light emitter;
wherein the plurality of distance sensors at least partially surrounds the image sensor.

2. The system of claim 1 wherein the registration device is fixedly coupled to an operating table.

3. The system of claim 1 wherein the plurality of actuators move the image sensor relative to a face of a patient.

4. The system of claim 1 wherein the plurality of actuators comprises a vertical actuator, a lateral actuator, and a longitudinal actuator.

5. The system of claim 1 wherein the registration device comprises a mechanically adjustable arm.

6. The system of claim 5 wherein the mechanically adjustable arm is adjustable in at least six directions.

7. The system of claim 1 wherein the pre-operative image comprises a computed tomography image.

8. The system of claim 1 wherein the plurality of distance sensors comprise infrared sensors.

9. The system of claim 1 wherein the controller determines a plurality of registration features from the registration data and compares pre-operative images to the plurality of registration features.

10. The system of claim 9 wherein the registration features comprise anthropometric points on a face of the patient.

11. The system of claim 1 wherein the controller controls an indicator based on comparing, said indicator comprising at least one of an audible indicator or a visual indicator.

12. The system of claim 1 wherein the controller compares the registration image to the pre-operative image, said controller generating a first indicator when the patient is in the registration position and a second indicator different than the first indicator when the patient is not in the registration position.

13. The system of claim 1 wherein the controller is programmed to move the actuators to move a facial scanner as the imaging portion relative to a face of the patient.

14. A method comprising:
receiving a pre-operative image of a patient;
controlling a plurality of actuators to move a registration device having an imaging portion relative to the patient;
generating registration data from a registration image from the portion of the registration device;
comparing the registration data and the pre-operative image;
outputting an indication based on the comparing:
monitor patient movement with the registration device; and
re-register the patient if it is determined that the patient moved using the registration device.

15. The method of claim 14 further comprising fixing the registration device relative to an operating table.

16. The method of claim 14 wherein controlling the plurality of actuators comprises controlling the plurality of actuators to move an image sensor relative to a face of the patient.

17. The method of claim 14 wherein generating the registration image comprises generating the registration image after acquiring the pre-operative image.

18. The method of claim 14 wherein outputting the indication based on the comparing includes generating a first indication when the patient is not registered to the pre-operative image and generating a second indication different than the first indication when the patient is registered to the pre-operative image.

* * * * *